US010359916B2

(12) United States Patent
Masumoto

(10) Patent No.: US 10,359,916 B2
(45) Date of Patent: Jul. 23, 2019

(54) VIRTUAL OBJECT DISPLAY DEVICE, METHOD, PROGRAM, AND SYSTEM

(71) Applicant: FUJIFILM Corporation, Tokyo (JP)

(72) Inventor: Jun Masumoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/670,472

(22) Filed: Aug. 7, 2017

(65) Prior Publication Data

US 2017/0357397 A1 Dec. 14, 2017

Related U.S. Application Data

(63) Continuation of application No. PCT/JP2016/051871, filed on Jan. 22, 2016.

(30) Foreign Application Priority Data

Feb. 16, 2015 (JP) ................................ 2015-027390

(51) Int. Cl.
*G06F 3/0484* (2013.01)
*G02B 27/01* (2006.01)
(Continued)

(52) U.S. Cl.
CPC ............ *G06F 3/0484* (2013.01); *A61B 90/20* (2016.02); *G02B 27/0172* (2013.01);
(Continued)

(58) Field of Classification Search
CPC ........ G06F 3/0484; G06F 3/011; G06F 3/014; G06F 3/04817; G06F 2203/04802;
(Continued)

(56) References Cited

U.S. PATENT DOCUMENTS 6,020,891 A 2/2000 Rekimoto
2011/0029903 A1 2/2011 Schooleman et al.
(Continued)

FOREIGN PATENT DOCUMENTS

JP 10-51711 A 2/1998
JP 2006-12042 A 1/2006
(Continued)

OTHER PUBLICATIONS

Japanese Notification of Reasons for Refusal for corresponding Japanese Application No. 2015-027390, dated Nov. 28, 2017, with English translation.

(Continued)

*Primary Examiner* — Chong Wu
(74) *Attorney, Agent, or Firm* — Birch, Stewart, Kolasch & Birch, LLP

(57) ABSTRACT

A camera 14 acquires a background image B0, and a virtual object acquisition unit 22 acquires a virtual object S0. A display information acquisition unit 23 acquires display information indicating a position, at which the virtual object S0 is displayed, from the background image B0, and a display control unit 24 displays the virtual object S0 on a display 15 based on the display information. A change information acquisition unit 25 acquires change information for changing the display state of the virtual object S0 according to the relative relationship between a reference marker image 36 and each of the other marker images 37, among a plurality of marker images 36 and 37 for changing the display state of the virtual object S0 that are included in the background image B0. A display state change unit 26 changes the display state of the virtual object according to the change information.

18 Claims, 12 Drawing Sheets

(51) Int. Cl.

| | |
|---|---|
| ***G06T 19/00*** | (2011.01) |
| ***G06T 19/20*** | (2011.01) |
| ***G06F 3/01*** | (2006.01) |
| ***G06F 3/0481*** | (2013.01) |
| ***G16H 40/63*** | (2018.01) |
| ***G16H 20/40*** | (2018.01) |
| ***A61B 90/20*** | (2016.01) |

(52) U.S. Cl.
CPC .............. *G06F 3/011* (2013.01); *G06F 3/014* (2013.01); *G06F 3/04817* (2013.01); *G06T 19/006* (2013.01); *G06T 19/20* (2013.01); *G16H 20/40* (2018.01); *G16H 40/63* (2018.01); *G02B 2027/0141* (2013.01); *G02B 2027/0178* (2013.01); *G06F 2203/04802* (2013.01); *G06T 2219/2012* (2013.01); *G06T 2219/2024* (2013.01)

(58) Field of Classification Search
CPC ........ G02B 27/0172; G02B 2027/0178; G02B 2027/0141; G06T 19/006; G06T 19/20; G06T 2219/2012; G06T 2219/2024; A61B 90/20; G16H 20/40; G16H 40/63
See application file for complete search history.

(56) References Cited

U.S. PATENT DOCUMENTS

| | | | | |
|---|---|---|---|---|
| 2012/0256950 | A1 | 10/2012 | Masuda et al. | |
| 2014/0132605 | A1* | 5/2014 | Tsukagoshi | ............ A61B 6/466 345/424 |
| 2014/0286574 | A1 | 9/2014 | Ota | |
| 2015/0170419 | A1 | 6/2015 | Ohashi | |

FOREIGN PATENT DOCUMENTS

| | | | |
|---|---|---|---|
| JP | 2010-26818 | A | 2/2010 |
| JP | 2011-521318 | A | 7/2011 |
| JP | 2011-198150 | A | 10/2011 |
| JP | 2013-105330 | A | 5/2013 |
| JP | 2013-172432 | A | 9/2013 |
| JP | 2014-10664 | A | 1/2014 |
| JP | 2014-155207 | A | 8/2014 |
| JP | 2014-186507 | A | 10/2014 |
| WO | WO 2012/081194 | A1 | 6/2012 |

OTHER PUBLICATIONS

International Preliminary Report on Patentability and Written Opinion of the International Searching Authority (forms PCT/IB/373 and PCT/ISA/237), dated Aug. 22, 2017, for corresponding International Application No. PCT/JP2016/051871, with an English translation of the Written Opinion.

International Search Report (form PCT/ISA/210), dated Feb. 16, 2016, for corresponding International Application No. PCT/JP2016/051871, with an English translation.

* cited by examiner

VIRTUAL OBJECT DISPLAY DEVICE, METHOD, PROGRAM, AND SYSTEM

CROSS-REFERENCE TO RELATED APPLICATIONS

This application is a Continuation of PCT International Application No. PCT/JP2016/051871 filed on Jan. 22, 2016, which claims priority under 35 U.S.C § 119(a) to Patent Application No. 2015-027390 filed in Japan on Feb. 16, 2015, all of which are hereby expressly incorporated by reference into the present application.

BACKGROUND OF THE INVENTION

1. Field of the Invention

The present invention relates to a virtual object display device, method, non-transitory computer readable recording medium storing a program, and system capable of changing the display state of a virtual object when displaying the virtual object using augmented reality, for example.

2. Description of the Related Art

In recent years, a display system has been proposed that uses augmented reality that makes a virtual object appear as if it is present in real space by superimposing the virtual object on a real-time background image obtained by imaging the real space and displaying the result on a display device, such as a head mount display. In such a system, a marker that specifies a position where a virtual object is to be displayed is disposed in the real space. Then, the marker is detected from the background image obtained by imaging the real space. In addition, a display position, a display size, and a display direction of the virtual object are determined according to the position, size, and direction of the detected marker, and the virtual object is displayed on the display device according to the determined display position, size, and direction. As a marker, an image, such as a two-dimensional barcode, is used. In addition, a method using a light emission diode (LED) or a finger of an operator as a marker has also been proposed.

On the other hand, it is also possible to perform a certain operation on the displayed virtual object. For example, a method has been proposed in which a marker with various patterns drawn is imaged and an event associated with the pattern occurs when the marker displayed using augmented reality comes into contact with a virtual object (refer to JP2011-198150A). In the method disclosed in JP2011-198150A, an event occurs in which the displayed virtual object is deleted or replaced with another virtual object. In addition, a method in which a finger of an operator is included in a background image and the finger is moved like a cursor to operate a virtual object (refer to JP2013-105330A), a method in which an operation interface for operating a virtual object is displayed using augmented reality and a virtual object is operated using the displayed operation interface (refer to JP2013-172432A), and the like have been proposed.

In the medical field, attendees of surgery gather before the surgery, and a preoperative conference is held to explain the surgery. In such a preoperative conference, in recent years, the surgery is simulated by displaying a part as a surgery target using augmented reality. For example, in partial resection surgery of the liver, a virtual object of the liver is generated by extracting tissues, such as liver, a portal vein, a vein, an artery, a body surface, a bone, and a tumor, from tomographic images of a three-dimensional image obtained from a computed tomography (CT) image or a magnetic resonance imaging (Mill) image and visualizing these as a three-dimensional image. Then, the virtual object is displayed in an actual size using the augmented reality, and a lead surgeon who is the representative of the preoperative conference explains the surgery to the attendees of the conference and simulates the surgery using the displayed virtual object. At this time, each attendee of the conference wears a display device, such as a head mount display, so that everyone can hold the conference while watching the same virtual object.

In applications of the display system using such augmented reality to the medical field, a method has been proposed in which a virtual object of a surgery target and an actual object, such as a medical instrument, are superimposed on the head mount display and display and non-display of the virtual object are switched according to the instruction of the operator or the virtual object is enlarged or reduced according to a distance from the object (refer to JP2014-155207A). A method has also been proposed in which a virtual object is displayed on a head mount display to be worn by each person, an object such as a scalpel is detected, and enlargement, transmissive display, and the like of the virtual object are switched by operating the object (refer to WO2012/081194A). When displaying a virtual object with a marker as a reference, a method has been proposed in which a plurality of markers are displayed and a position, a direction and an inclination are changed for each corresponding object by moving the marker (refer to JP2014-010664A).

SUMMARY OF THE INVENTION

Incidentally, by changing the display state such as the color, brightness, and opacity of a virtual object displayed using the augmented reality, it is possible to display the virtual object in various display states. In this case, it is conceivable to change the display state of the virtual object by performing an operation based on the methods disclosed in JP2011-198150A, JP2013-105330A, and JP2013-172432A.

However, in the methods disclosed in JP2011-198150A and JP2013-105330A, an operation is performed on a virtual object displayed using the augmented reality by moving a finger or the like, which is further projected on the screen, toward the virtual object. For this reason, if the position of the displayed virtual object changes due to a change in the direction of the face of the operator or the like, it becomes difficult to perform an operation for moving an image, such as a finger. When the virtual object is displayed small, the amount of operation of a finger or the like for the operation is reduced. Accordingly, it becomes more difficult to perform an operation for moving a finger or the like. In the method disclosed in JP2013-172432A, since an operation interface is also displayed using augmented reality, the operation is not performed on an object but performed on the space. For this reason, there is no real feeling, such as pressing a button, and it is difficult to perform an operation for minutely changing the display state. Therefore, it is conceivable to use hardware, such as an input device for changing the display state of a virtual object. In this case, however, it is necessary to separately prepare hardware, and a complicated application for changing the display state of a virtual object using the hardware is required.

Also in the methods disclosed in JP2014-155207A, WO2012/081194A, and JP2014-010664A, the virtual object is enlarged or reduced and display and non-display are switched according to the distance between the object and the virtual object or the distance between a plurality of markers. However, as in the methods disclosed in JP2011-198150A and JP2013-105330A, if the position of the displayed virtual object changes due to a change in the direction of the face of the operator or the like, it becomes difficult to perform an operation for change. In addition, it is difficult to perform an operation for minutely changing the display state of the virtual object.

The present invention has been made in view of the above-described circumstances, and the object of the present invention is to make it possible to change the display state of a virtual object with high accuracy.

A virtual object display device according to the present invention comprises: an imaging unit that acquires a background image; a virtual object acquisition unit that acquires a virtual object; a display unit that displays the virtual object; a display information acquisition unit that acquires display information indicating a position, at which the virtual object is displayed, from the background image; a display control unit that displays the virtual object on the display unit based on the display information; a change information acquisition unit that acquires change information for changing a display state of the virtual object according to a relative relationship between a reference marker image showing a reference marker as a reference and each of other marker images showing other markers other than the reference marker, among a plurality of marker images that show a plurality of markers for changing the display state of the virtual object and that are included in the background image; and a display state change unit that changes the display state of the virtual object according to the change information.

The "background image" is an image as a background to display the virtual object, for example, an image in real space. The background image is a motion picture obtained by sequentially imaging the background to display the virtual object at predetermined sampling intervals.

The "display information" refers to information that is included in the background image by imaging an object for displaying the virtual object, which is placed at a position where the virtual object is displayed, when necessary, placed in real space in order to specify at least one of the size or the direction. As examples of the object for displaying the virtual object, a two-dimensional barcode, a marker having a color or a pattern given thereto, a marker such as an LED, some instruments, a part of the body such as an operator's finger, an edge of an object included in the background image, and a feature point such as an intersection between edges can be used. In the case of using a marker, the display information is acquired from the marker image showing the marker included in the background image.

Here, when the reference marker and another marker are aligned and another marker is rotated, moved, or moved closer to or away from the imaging unit, another marker image rotates or moves relative to the reference marker image, or their sizes become different. When a color is given to the reference marker and the color of another marker is changed, the color of another marker image changes relative to the reference marker image. When a certain pattern is given to the reference marker and the pattern of another marker is changed, the pattern of another marker images changes relative to the reference marker image. The "relative relationship" means the relative angle change, distance change, size change, color change, pattern change, and the like of another marker image with respect to the reference marker image.

"Changing the display state" means changing the state of the virtual object appealing to the visual sense of the viewer of the virtual object. For example, "changing the display state" means changing the color, brightness, contrast, opacity, sharpness, and the like of the virtual object. In the case of a virtual object whose form is changed with the passage of time by applying a hand to the virtual object, changes in form with the passage of time are also included in the change of the display state. In a case where the virtual object is configured to include a plurality of objects, the display state may be changed for each of the objects.

In the virtual object display device according to the present invention, the background image may be acquired by imaging a background corresponding to a viewing field of a user.

In the virtual object display device according to the present invention, the display information may further include at least one of a size or a direction when displaying the virtual object.

In the virtual object display device according to the present invention, the display unit may combine the virtual object with the background image and display a result of the combination.

In the virtual object display device according to the present invention, the display information acquisition unit may acquire the display information from a marker image that shows a marker for displaying the virtual object and that is included in the background image by imaging the marker for displaying the virtual object.

In the virtual object display device according to the present invention, the display information acquisition unit may acquire the display information from the reference marker image that is included in the background image by imaging the reference marker.

The virtual object display device according to the present invention may further comprise a setting amount display control unit that displays information indicating a setting amount of the display state of the virtual object on the display unit.

The "information indicating a setting amount" is information from which the setting amount of the display state of the virtual object being displayed can be recognized by viewing it. For example, information capable of indicating the setting amount, such as a numerical value, a pie chart, a bar graph, and a scale with gradations indicating the setting amount can be used as the "information indicating a setting amount".

In the virtual object display device according to the present invention, the setting amount display control unit may display information indicating the setting amount in vicinity of a plurality of marker images showing a plurality of markers for changing the display state of the virtual object.

"Vicinity" means a distance at which both a plurality of marker images and the information indicating the setting amount can be observed to some extent without moving the line of sight. In addition, "vicinity" includes both a case where a plurality of marker images and the information indicating the setting amount are in contact with each other and a case where a plurality of marker images and the information indicating the setting amount are superimposed on each other.

In the virtual object display device according to the present invention, each of the markers for changing the display state of the virtual object may be a polyhedron having surfaces to which information for changing the display state is given.

In the virtual object display device according to the present invention, the polyhedron may be a cube.

In the virtual object display device according to the present invention, the virtual object may include a plurality of objects, the change information acquisition unit may acquire change information for a plurality of objects for changing a display state of each of the plurality of objects, the display state change unit may change the display state for each of the plurality of objects according to the change information for objects, and the setting amount display unit may display information indicating a setting amount of each of the plurality of objects on the display unit for each of the plurality of objects.

In the virtual object display device according to the present invention, the virtual object may be a three-dimensional image.

In particular, the three-dimensional image may be a medical three-dimensional image.

In the virtual object display device according to the present invention, the display unit may be an eyeglass type display device.

As the "eyeglass type display device", for example, a head mount display and a display device of an eyeglass-type wearable terminal can be mentioned. The "eyeglass type display device" may be of an immersive type that completely covers the eyes or a transmissive type that allows seeing the surrounding situation.

A virtual object display system according to the present invention comprises a plurality of the virtual object display devices according to the present invention that correspond to a plurality of users. The display state change unit in each of the plurality of virtual object display devices changes the display state of the virtual object according to change information acquired by the change information acquisition unit of any one of the virtual object display devices.

Another virtual object display system according to the present invention comprises a plurality of the virtual object display devices according to the present invention that correspond to a plurality of users. The display state change unit in each of the plurality of virtual object display devices changes the display state of the virtual object according to change information acquired by the change information acquisition unit of each of the virtual object display devices.

A virtual object display method according to the present invention comprising: acquiring a background image; acquiring a virtual object; acquiring display information indicating a position, at which the virtual object is displayed, from the background image; displaying the virtual object on the display unit based on the display information; acquiring change information for changing a display state of the virtual object according to a relative relationship between a reference marker image showing a reference marker as a reference and each of other marker images showing other markers other than the reference marker, among a plurality of marker images that show a plurality of markers for changing the display state of the virtual object and that are included in the background image; changing the display state of the virtual object according to the change information; and displaying information indicating a setting amount of the display state of the virtual object on the display unit.

In addition, a non-transitory computer readable recording medium storing a program causing a computer to execute the virtual object display method according to the present invention may be provided.

According to the present invention, a virtual object is displayed based on the display information, and the change information for changing the display state of the virtual object is acquired according to the relative relationship between the reference marker image showing a reference marker as a reference and each of other marker images showing other markers other than the reference marker, among a plurality of marker images that show a plurality of markers for changing the display state of the virtual object and that are included in the background image. Then, the display state of the virtual object is changed according to the change information. Therefore, by simply changing the relative relationship between the reference marker and each of the other markers, it is possible to change the display state of the virtual object. As a result, it is possible to accurately change the display state of the virtual object according to the actual operation.

DESCRIPTION OF THE PREFERRED EMBODIMENTS

Figure 1:
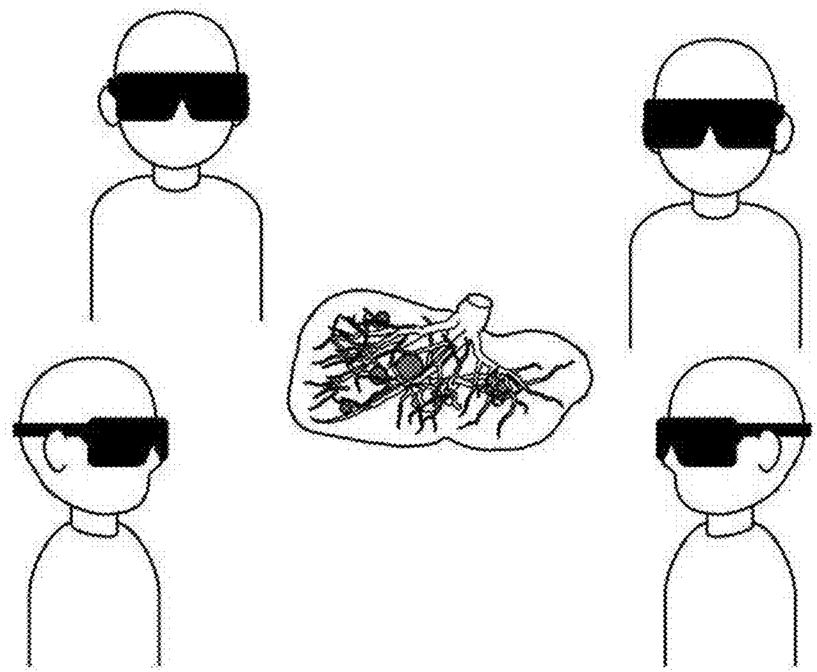
FIG. 1 is a diagram illustrating how a virtual object display device according to a first embodiment of the present invention is used.

Hereinafter, embodiments of the present invention will be described with reference to the diagrams. FIG. 1 is a diagram illustrating how a virtual object display device according to a first embodiment of the present invention is used. The virtual object display device according to the first embodiment is for displaying a three-dimensional image of the liver, which is a surgery target, as a virtual object using augmented reality in a preoperative conference. Specifically, the virtual object display device according to the first embodiment is used in a situation where a three-dimensional image of the liver is generated as a virtual object from a three-dimensional image obtained by imaging a subject, each attendee of surgery wears a head mount display (hereinafter, referred to as an HMD) in a preoperative conference, and a virtual object is displayed on the HMD to receive various surgical explanations regarding the surgery from a lead surgeon who is the representative of the preoperative conference. The virtual object display device according to the present invention is included in the HMD.

Figure 2:
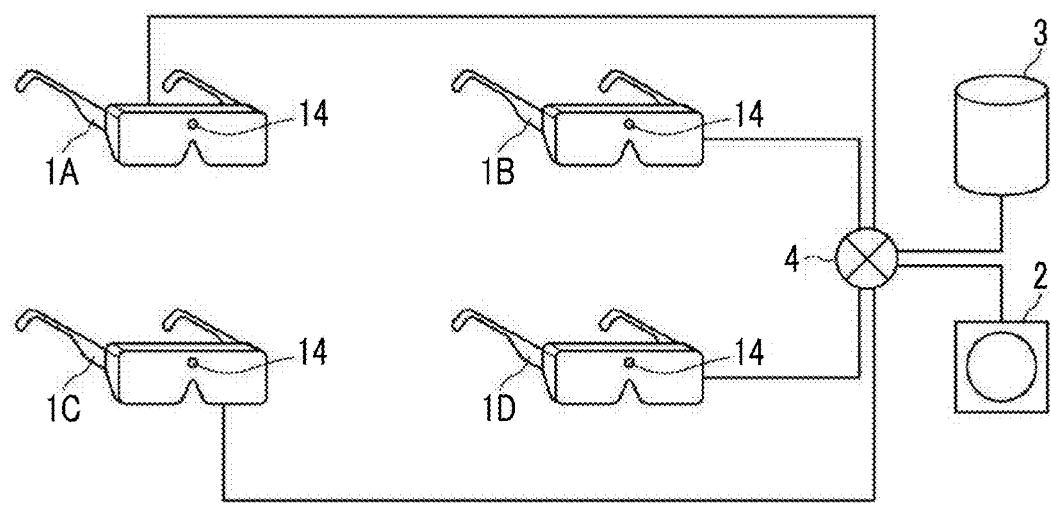
FIG. 2 is a hardware configuration diagram showing the outline of a virtual object display system to which the virtual object display device according to the first embodiment is applied.

FIG. 2 is a hardware configuration diagram showing the outline of a virtual object display system to which the virtual object display device according to the first embodiment is applied. As shown in FIG. 2, in this system, a plurality of (four in the present embodiment) HMDs 1A to 1D including the virtual object display device according to the first embodiment, a three-dimensional imaging apparatus 2, and an image storage server 3 are communicably connected to each other through a network 4. Even between the HMDs 1A to 1D, information can be exchanged through the network 4. Each of the HMDs 1A to 1D corresponds to a virtual object display device of the present invention. In the following explanation, the four HMDs 1A to 1D may be represented by the HMD 1.

The three-dimensional imaging apparatus 2 is an apparatus that generates a three-dimensional image V0 showing a part, which is a surgery target in a subject, by imaging the part. Specifically, the three-dimensional imaging apparatus 2 is a CT apparatus, an MRI apparatus, a positron emission tomography (PET) apparatus, or the like. The three-dimensional image V0 generated by the three-dimensional imaging apparatus 2 is transmitted to be stored in the image storage server 3. In the present embodiment, it is assumed that the surgery target part of the subject is the liver, the three-dimensional imaging apparatus 2 is a CT apparatus, and the three-dimensional image V0 of the abdomen is generated.

The image storage server 3 is a computer that stores and manages various kinds of data, and includes a large-capacity external storage device and software for database management. The image storage server 3 performs communication with other devices through the wired or wireless network 4 to transmit and receive image data or the like. Specifically, the image storage server 3 acquires image data, such as the three-dimensional image V0 generated by the three-dimensional imaging apparatus 2, through the network, and stores the image data in a recording medium, such as a large-capacity external storage device, and manages the image data. The storage format of image data or the communication between devices through the network 4 is based on a protocol, such as a digital imaging and communication in medicine (DICOM).

The HDM 1 includes a computer, and a virtual object display program of the present invention is installed on the computer. The virtual object display program is installed in a memory of the HMD 1. Alternatively, the virtual object display program is stored in a storage device of a server computer connected to the network or in a network storage so as to be accessible from the outside, and is downloaded and installed into the HMD 1 when necessary.

Figure 3:
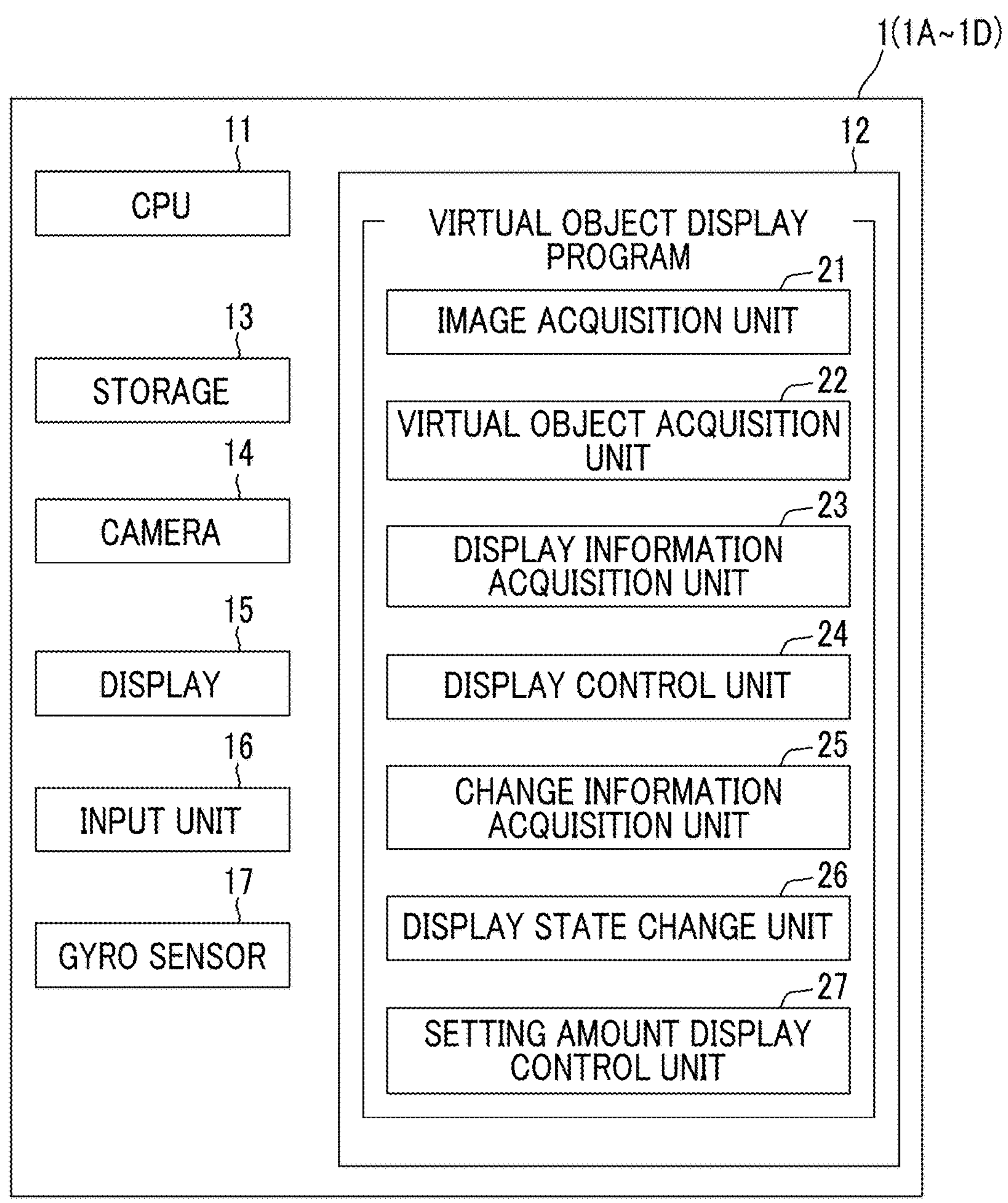
FIG. 3 is a block diagram showing the schematic configuration of a head mount display that is a virtual object display device.

FIG. 3 is a block diagram showing the schematic configuration of the HMD 1 that is a virtual object display device realized by installing a virtual object display program. As shown in FIG. 3, the HMD 1 includes a central processing unit (CPU) 11, a memory 12, a storage 13, a camera 14, a display 15, and an input unit 16. A gyro sensor 17 for detecting the movement of the head of the wearer of the HMD 1 is also provided. The camera 14 corresponds to imaging unit of the present invention, and the display 15 corresponds to the display unit of the present invention. The camera 14, the display 15, and the gyro sensor 17 may be provided in a portion of the HMD 1 to be attached to the head, and the memory 12, the storage 13, and the input unit 16 may be provided separately from the attachment portion.

Various kinds of information including the three-dimensional image V0, which has been acquired from the image storage server 3 through the network 4, and the image generated by the processing in the HMD 1 are stored in the storage 13.

The camera 14 includes a lens, an imaging device such as a charge coupled device (CCD), an image processing unit that performs processing for improving the image quality of the acquired image, and the like. As shown in FIG. 2, the camera 14 is attached to the HMD 1 so as to be located in a portion corresponding to the center of the eyes of the attendee in the HMD 1. Accordingly, when the attendee of the preoperative conference wears the HMD 1, the viewing field of the wearer and the imaging range of the camera 14 match each other. Therefore, when the attendee wears the HMD 1, the camera 14 captures an image corresponding to the viewing field of the attendee, and acquires an image of real space that the attendee is watching as a background image B0. The background image B0 is a motion picture having a predetermined frame rate.

The display 15 is configured to include a liquid crystal panel for displaying the background image B0 and a virtual object S0 and the like. The display 15 includes a display unit for the left eye and a display unit for the right eye of the wearer of the HMD 1.

The input unit 16 is configured to include, for example, button and the like, and is provided at a predetermined position of the exterior of the HMD 1.

A virtual object display program is stored in the memory 12. The virtual object display program specifies as processing to be executed by the CPU 11, image acquisition processing of the three-dimensional image V0 acquired by the three-dimensional imaging apparatus 2 and the background image B0 acquired by the camera 14, virtual object acquisition processing for acquiring a virtual object, display information acquisition processing for acquiring display information indicating the position, size, and direction for displaying the virtual object from the background image B0, display control processing for displaying the background image B0 on the display 15 and displaying the virtual object on the display 15 based on the display information, change information acquisition processing for acquiring change information for changing the display state of the virtual object from the background image B0, display state change processing for changing the display state of the virtual object according to the change information, and setting amount display control processing for displaying information indicating the setting amount of the display state of the virtual object on the display 15.

The CPU 11 executes these processes according to the program, so that the HMD 1 functions as an image acquisition unit 21, a virtual object acquisition unit 22 (virtual object acquisition means), a display information acquisition unit 23 (display information acquisition means), a display control unit 24 (display control means), a change information acquisition unit 25 (change information acquisition means), a display state change unit 26 (display state change means), and a setting amount display control unit 27 (setting amount display control means). The HMD 1 may include processing devices that respectively perform image acquisition processing, virtual object acquisition processing, display information acquisition processing, display control processing, change information acquisition processing, display state change processing, and setting amount display control processing.

The image acquisition unit 21 acquires the three-dimensional image V0 and the background image B0 captured by the camera 14. In a case where the three-dimensional image V0 is already stored in the storage 13, the image acquisition unit 21 may acquire the three-dimensional image V0 from the storage 13.

The virtual object acquisition unit 22 generates a three-dimensional image of the liver, which is a surgery target part, as a virtual object. Accordingly, the virtual object acquisition unit 22 first extracts the liver, which is a surgery target part, and arteries, veins, portal veins, and lesions, which are included in the liver, from the three-dimensional image V0. The virtual object acquisition unit 22 includes an identifier for identifying whether or not each pixel in the three-dimensional image V0 is a pixel showing the liver and arteries, veins, portal veins, and lesions included in the liver (hereinafter, referred to as the liver and the like). The identifier acquires a plurality of sample images including the liver and the like by machine learning using a method, such as Ada boosting algorithm. The virtual object acquisition unit 22 extracts the liver and the like from the three-dimensional image V0 using the identifier.

Then, the virtual object acquisition unit 22 generates an image showing the three-dimensional shape of the liver and the like as a virtual object display S0. Specifically, a projected image obtained by projecting the extracted liver and the like onto a projection plane defined by display information to be described late is generated as the virtual object S0. As a specific projection method, for example, a known volume rendering method is used.

Figure 4:
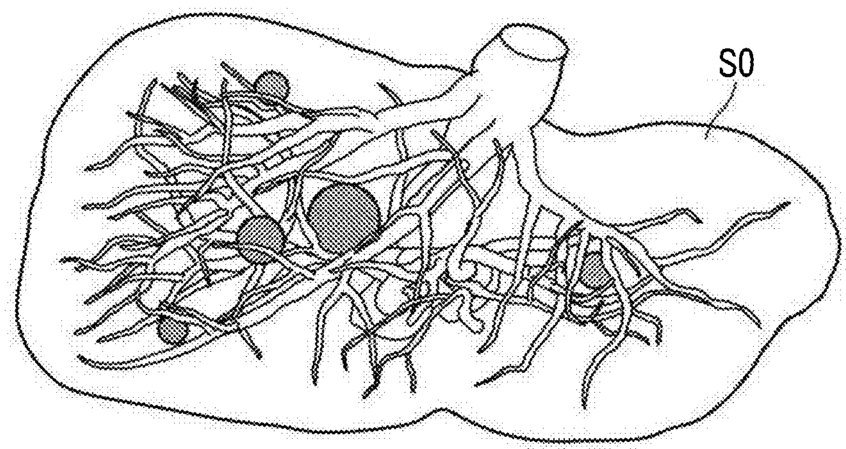
FIG. 4 is a diagram showing an example of a virtual object.

At this time, the virtual object S0 may be generated by defining different colors for the liver and arteries, veins, portal veins, and lesions included in the liver, or the virtual object S0 may be generated by defining different opacities. For example, the artery may be red, the vein may be blue, the portal vein may be green, and the lesion may be yellow. The opacity of the liver may be set to 0.1, the opacities of the artery, the vein, and the portal vein may be set to 0.5, and the opacity of the lesion may be set to 0.8. As a result, the virtual object S0 shown in FIG. 4 is generated. Thus, by defining different colors or different opacities for the liver and arteries, veins, portal veins, and lesions, which are included in the liver, in the virtual object S0, it is possible to easily identify the liver and arteries, veins, portal veins, and lesions included in the liver. Alternatively, the virtual object S0 may be generated by defining both different colors and different opacities. The generated virtual object S0 is stored in the storage 13.

The virtual object S0 may be generated from the three-dimensional image V0 by a virtual object generation device (not shown), and may be stored in the image storage server 3. In this case, the virtual object acquisition unit 22 acquires the virtual object S0 from the image storage server 3.

Figure 5:
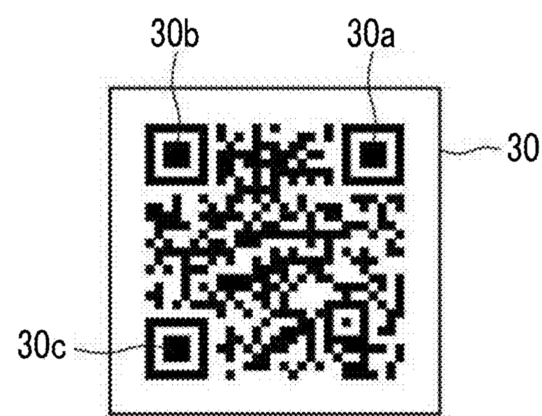
FIG. 5 is a diagram showing the first marker.
Figure 6:
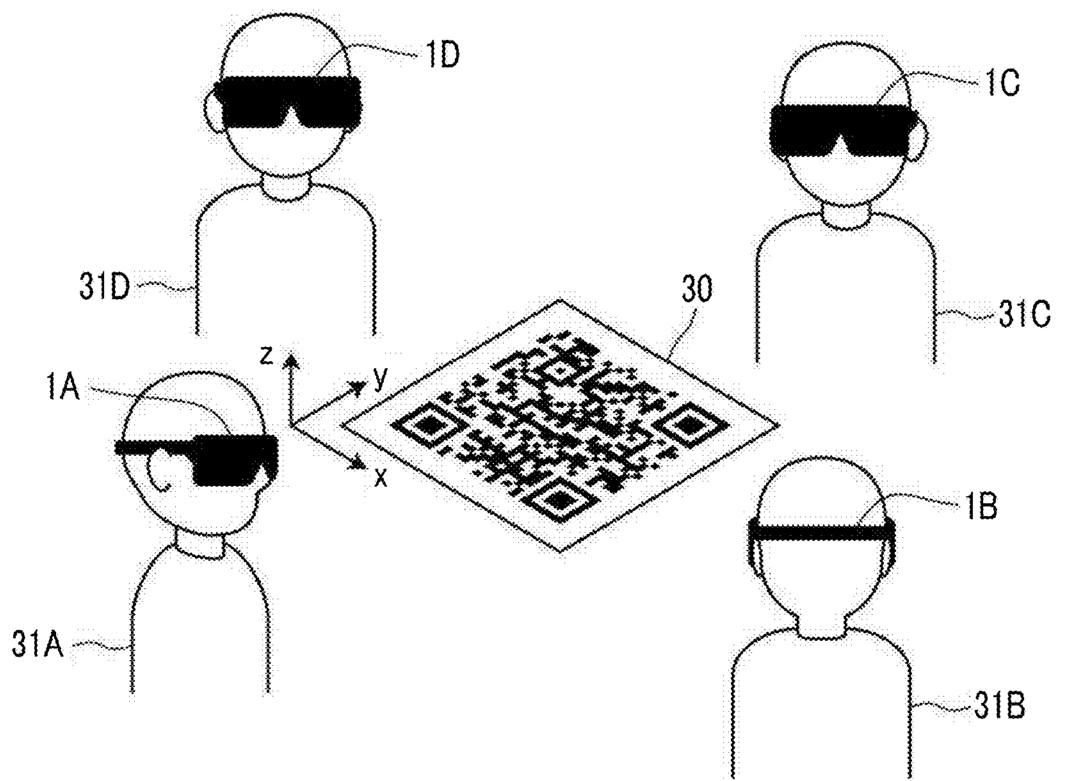
FIG. 6 is a diagram showing a first marker placed at a location where a preoperative conference is held.

The display information acquisition unit 23 acquires display information indicating the position, the size, and the direction for displaying the virtual object S0 from the background image B0. In the present embodiment, the display information is acquired from a marker image that shows a first marker and that is included in the background image B0 by imaging the first marker that is a virtual object display marker. FIG. 5 is a diagram showing a first marker. As shown in FIG. 5, a first marker 30 is formed by attaching a two-dimensional barcode to a flat plate. The first marker 30 may be one obtained by printing a two-dimensional barcode on paper. As shown in FIG. 6, the first marker 30 is placed at a location where a preoperative conference is held. Four attendees 31A to 31D wear the HMDs 1A to 1D, respectively. In the HMDs 1A to 1D, the background image B0 captured by the camera 14 is displayed on the display 15. Each attendee directs the line of sight in the direction of the first marker 30 so that a first marker image 31, which is an image of the first marker 30, is included in the background image B0 displayed on the display 15.

Figure 7:
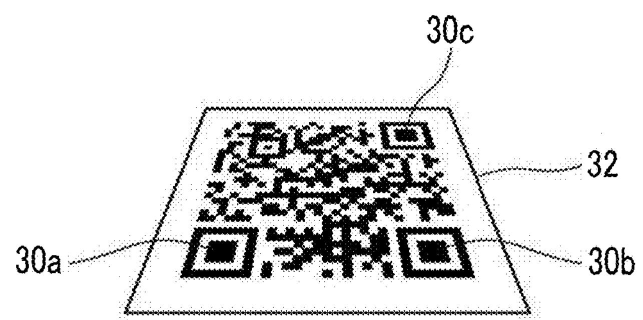
FIG. 7 is a diagram showing a first marker image extracted from a background image.

The display information acquisition unit 23 extracts the first marker image 31 showing the first marker 30 from the background image B0. FIG. 7 is a diagram showing the first marker image extracted from the background image B0. The first marker image shown in FIG. 7 is acquired by the HMD 1A of the attendee 31A. Here, the two-dimensional barcode of the first marker 30 includes three reference points 30*a* to 30*c* as shown in FIG. 5. The display information acquisition unit 23 detects the reference points 30*a* to 30*c* in an extracted first marker image 32. Then, from the positions of the detected reference points 30*a* to 30*c* and the distance between the reference points, a position, a size, and a direction when displaying the virtual object S0 are determined.

Here, in the present embodiment, a position whose the reference points 30*a* and 30*b* are seen side by side is defined as a front position when displaying the virtual object S0. Therefore, by detecting the positions of the reference points 30*a* and 30*b* in the first marker image 32, it is possible to determine a rotation position from the front position with respect to an axis perpendicular to the first marker 30 of the virtual object S0 (hereinafter, referred to as a z axis). In addition, it is possible to determine the size when displaying the virtual object S0 by the difference between the distance between the reference points 30*a* and 30*b* and the predetermined reference value. In addition, by a difference between a triangle having the reference points 30*a* to 30*c* as apices and the reference shape, it is possible to determine a rotation position from the reference position with respect to two axes (hereinafter, referred to as an x axis and a y axis) perpendicular to the z axis of the virtual object S0, that is, a direction. The display information acquisition unit 23 outputs the determined position, size, and direction of the virtual object S0 as display information.

Figure 8:
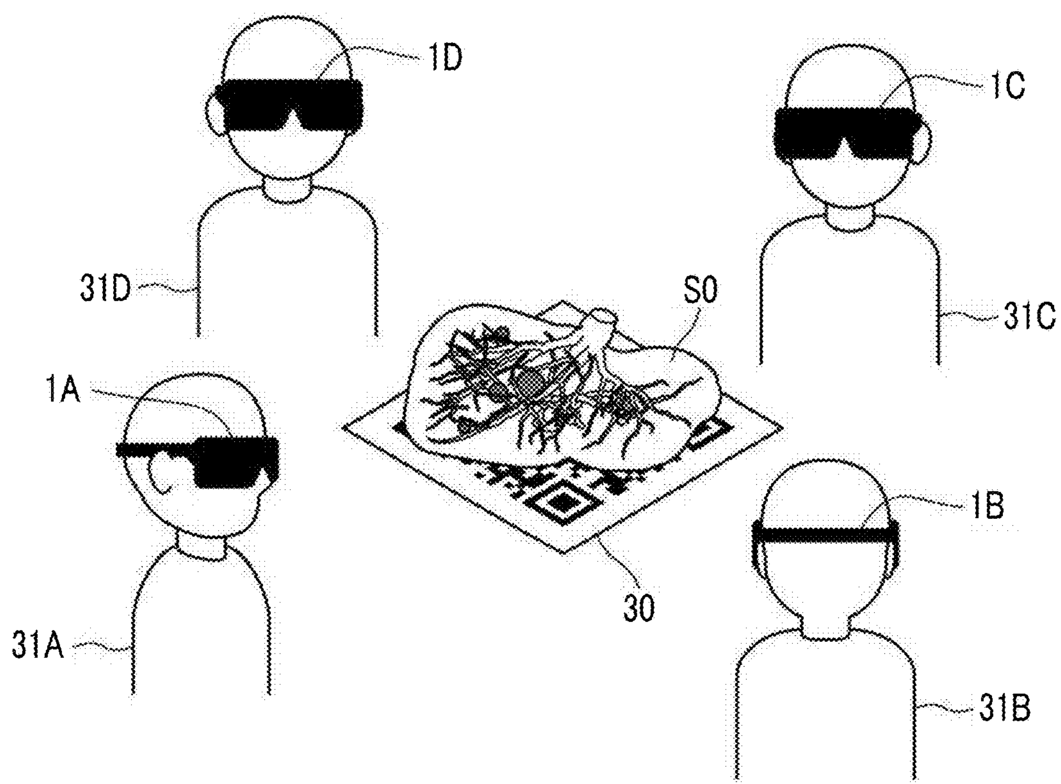
FIG. 8 is a diagram schematically showing the display state of a virtual object at a location where a preoperative conference is held.

Using the display information, the display control unit 24 specifies a projection plane onto which the virtual object S0 is projected, and projects the virtual object S0 onto the projection plane. Then, the projected virtual object S0 is superimposed on the background image B0, and the result is displayed on the display 15. FIG. 8 is a diagram schematically showing the display state of the virtual object S0 at a place where the preoperative conference is held. As shown in FIG. 8, on the display 15, the attendees 31A to 31D can observe a state in which a three-dimensional image of the liver having a size and a direction corresponding to the position of each attendee is displayed as the virtual object S0 on the first marker 30 in real space.

The display control unit 24 displays the virtual object S0 in a display unit for the left eye and a display unit for the right eye of the display 15 so as to have parallax. As a result, the attendee can stereoscopically view the virtual object S0.

By rotating or tilting the first marker 30 with respect to the z axis in this state, it is possible to change the direction of the virtual object S0 displayed on the display 15.

Figure 9:
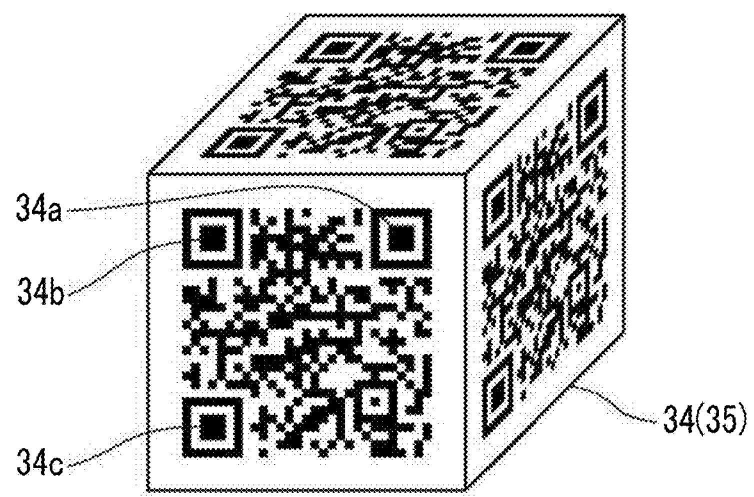
FIG. 9 is a diagram showing a second marker.

The change information acquisition unit 25 acquires change information for changing the display state of the virtual object from the background image B0. As the display state, it is possible to define the color, brightness, contrast, opacity, sharpness, and the like of the virtual object S0. In the present embodiment, it is assumed that the opacity is defined. In addition, in the present embodiment, the change information is acquired from a plurality of marker images that show a plurality of second markers and that are included in the background image B0 by imaging the plurality of second markers for changing the display state of the virtual object S0. FIG. 9 is a diagram showing one of the second markers. As shown in FIG. 9, a second marker 34 is formed by attaching a two-dimensional barcode to each surface of a cube. The second marker 34 may be one obtained by printing a two-dimensional barcode on each surface of a developed view of a cube and assembling the barcodes so as to be a cube. Here, in the present embodiment, it is assumed that two second markers 34 and 35 are used. The marker 34 corresponds to a reference marker, and the marker 35 corresponds to a marker other than the reference marker.

In the present embodiment, the opacity is defined as a display state in the two-dimensional barcodes attached to all surfaces. However, two-dimensional barcodes defining different display states for the respective surfaces may be attached. For example, in addition to the opacity, two-dimensional barcodes defining the color, brightness, and sharpness may be attached to the respective surfaces of the cube.

Figure 10:
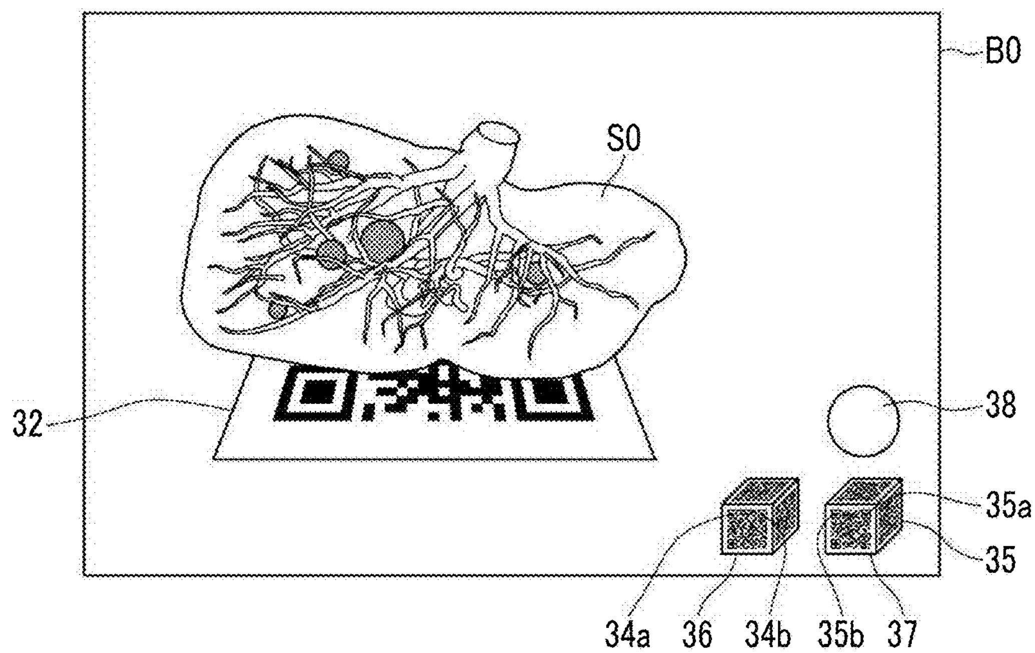
FIG. 10 is a diagram illustrating a change in the inclination of the second marker.

In the case of holding a preoperative conference, the second markers 34 and 35 are held by the lead surgeon who explains the surgery. The lead surgeon holds the second markers 34 and 35 so that the second markers 34 and 35 are included in the imaging range of the camera 14 of the HMD 1 worn by the lead surgeon. Any of the six surfaces of the second markers 34 and 35 may be projected onto the background image B0 from the front. Then, as shown in FIG. 10, marker images 36 and 37 of the second markers 34 and 35 are displayed on the display 15. The marker image 36 is used as a reference marker image, and the marker image 37 is used as another marker image. In the case of using the second markers 34 and 35 attached with two-dimensional barcodes defining different display states for the respective surfaces, the lead surgeon may hold the second markers 34 and 35 so that the two-dimensional barcode defining the display state to be changed is included in the background image B0.

Figure 11:
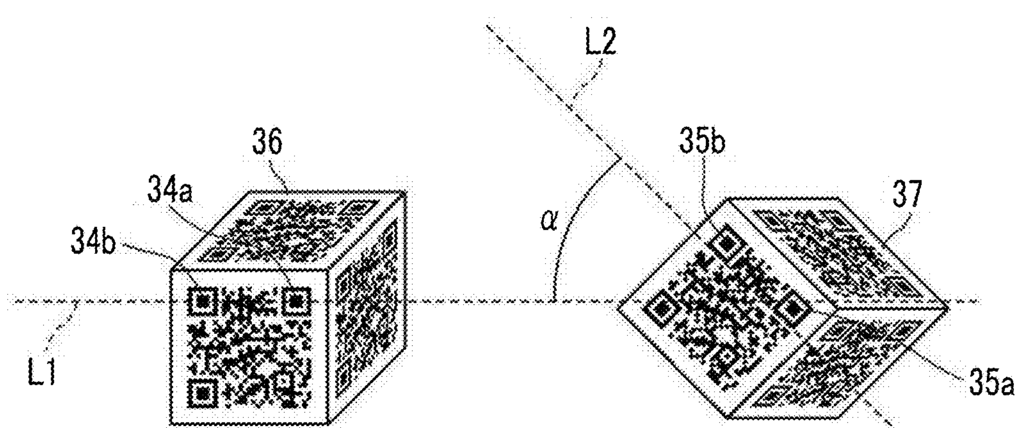
FIG. 11 is a diagram illustrating the acquisition of change information using two second markers.

The change information acquisition unit 25 extracts the second marker images 36 and 37 showing the second markers 34 and 35 from the background image B0. In the present embodiment, in order to change the display state of the virtual object S0, the lead surgeon changes the inclination of the other marker 35 with respect to the reference marker 34. FIG. 11 is a diagram illustrating a change in the inclination of the other marker 35 with respect to the reference marker 34.

In the present embodiment, it is assumed that the display state of the virtual object S0 is changed by rotating the other marker 35 clockwise with respect to the reference marker 34. Accordingly, the amount of change of the display state increases as the amount of rotation in the clockwise direction increases.

In the present embodiment, a straight line connecting reference points 34*a* and 34*b* to each other, among three reference points 34*a* to 34*c* included in the reference marker 34, is defined as a reference line, and the amount of change of the display state of the virtual object S0 is defined according to the angle of a straight line connecting reference points 35*a* and 35*b* to each other, among three reference points 35*a* to 35*c* included in the other marker 35, with respect to the reference line. Accordingly, the change information acquisition unit 25 detects the reference points 34*a* and 34*b* and the reference points 35*a* and 35*b* in the extracted second marker images 36 and 37. Then, a straight line connecting the detected reference points 34*a* and 34*b* to each other is defined as a reference line L1, and a straight line L2 connecting the reference points 35*a* and 35*b* to each other is defined. Then, an angle α of the straight line L2 with respect to the reference line L1 is calculated.

Here, in the present embodiment, only the change information acquisition unit 25 of the HMD 1 worn by the lead surgeon acquires the change information, and the acquired change information is transmitted to the HMD 1 worn by other attendees through the network 4.

The change information acquisition unit 25 acquires the ratio of the calculated angle α to 360° as change information. For example, in a case where the angle α is 0°, the change information is 0. In a case where the angle α is 90°, the change information is 0.25.

Figure 12:
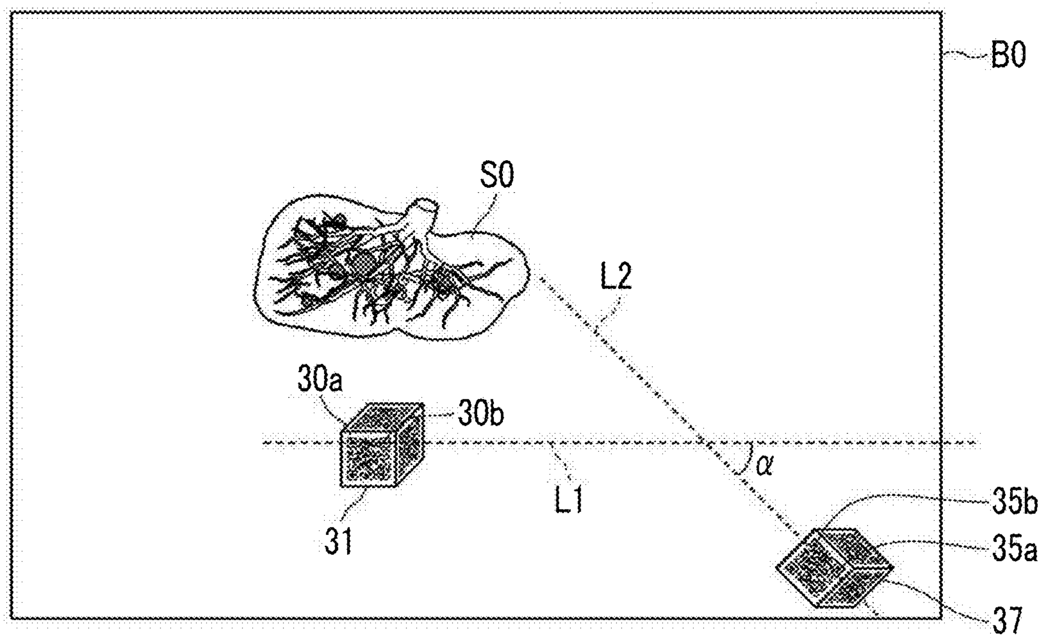
FIG. 12 is a diagram illustrating the acquisition of change information using first and second markers.

In addition, the first marker 30 may be one obtained by attaching a two-dimensional barcode to each surface of a cube similarly to the second markers 34 and 35, only one marker 35 may be prepared as a second marker, a relative angle of the straight line L2 calculated from the second marker image 37 with respect to the reference line L1 calculated from the first marker image 31 may be calculated, and change information may be acquired based on this. For example, as shown in FIG. 12, an angle α at which a straight line passing through the reference points 30*a* and 30*b* in the first marker image 31 crosses a straight line passing through the reference points 35*a* and 35*b* in the second marker image 37 may be calculated, and the ratio of the calculated angle to 360° may be acquired as change information.

In the first embodiment, both the second markers 34 and 35 may be operated in a state in which these are held by hand. However, the second marker 34 as a reference may be placed on a table or the like. Thus, since the other second marker 35 can be operated with one hand, an operation to change the display state becomes easy. Both of the second markers 34 and 35 may be placed on the table. In this case, since the second marker 35 rotates only in units of 90°, it is not possible to continuously change the display state, but it is not necessary to hold the second markers 34 and 35 at all times in hand.

The display state change unit 26 changes the display state of the virtual object S0 using the change information acquired by the change information acquisition unit 25. For example, in a case where the opacity in the initial state of the virtual object S0 is 1.00 and the change information is 0.25, the opacity is changed to 0.75.

Here, in a case where the angle α of the straight line L2 with respect to the reference line L1 for the second marker 35 is 0°, the display state of the virtual object S0 is not changed from the initial state. Then, when the second marker 35 is tilted so that the angle α of the straight line L2, which connects the reference points 35*a* and 35*b* to each other, with respect to the reference line L1 increases, the opacity of the virtual object S0 decreases.

Figure 13:
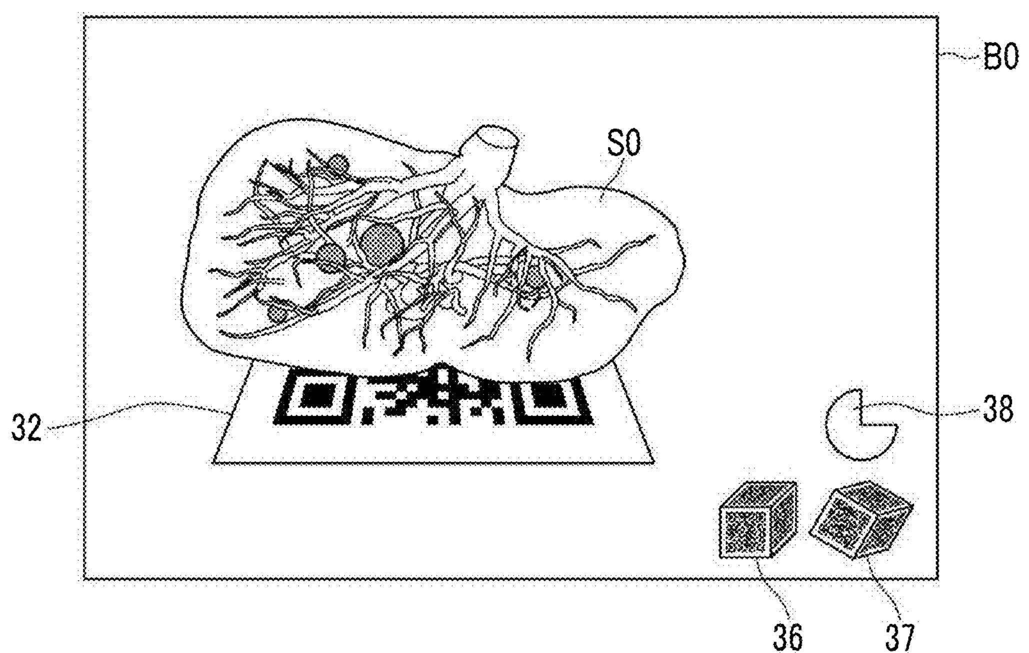
FIG. 13 is a diagram illustrating the display of information indicating the setting amount.
Figure 14:
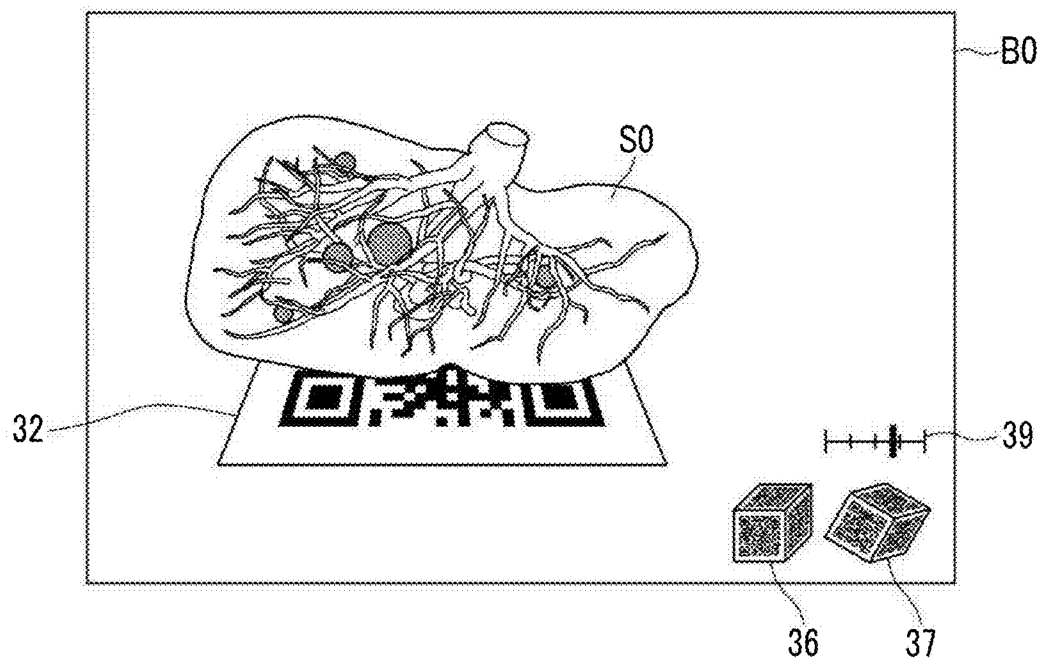
FIG. 14 is a diagram illustrating the display of information indicating the setting amount.

The setting amount display control unit 27 displays, on the display 15, information indicating the setting amount of the display state of the virtual object S0. In the present embodiment, a pie chart is used as the information indicating the setting amount. As shown in FIG. 10, the setting amount display control unit 27 displays a pie chart 38, as the information indicating the setting amount, above the second marker images 36 and 37. FIG. 10 shows the pie chart 38 in a case where the opacity is 1.00 as the initial state. However, in a case where the angle of the other marker 35 is changed to 90°, the change information becomes 0.25. Therefore, as shown in FIG. 13, the pie chart 38 indicates that the opacity is 0.75. Instead of the pie chart, a bar graph may be used, or a scale 39 with gradations may be used as shown in FIG. 14. Alternatively, a numerical value indicating the setting amount may be used. The display position of information indicating the setting amount is not limited to the upper side of the second marker images 36 and 37. As long as it is possible to recognize both the second marker images 36 and 37 and the information indicating the setting amount without moving the line of sight, the display position of information indicating the setting amount may be the left or right of the second marker images 36 and 37 or may be the lower side of the second marker images 36 and 37. The information indicating the setting amount may be superimposed on the second marker images 36 and 37. In addition, the information indicating the setting amount may be displayed at an arbitrary position of the display 15.

Figure 15:
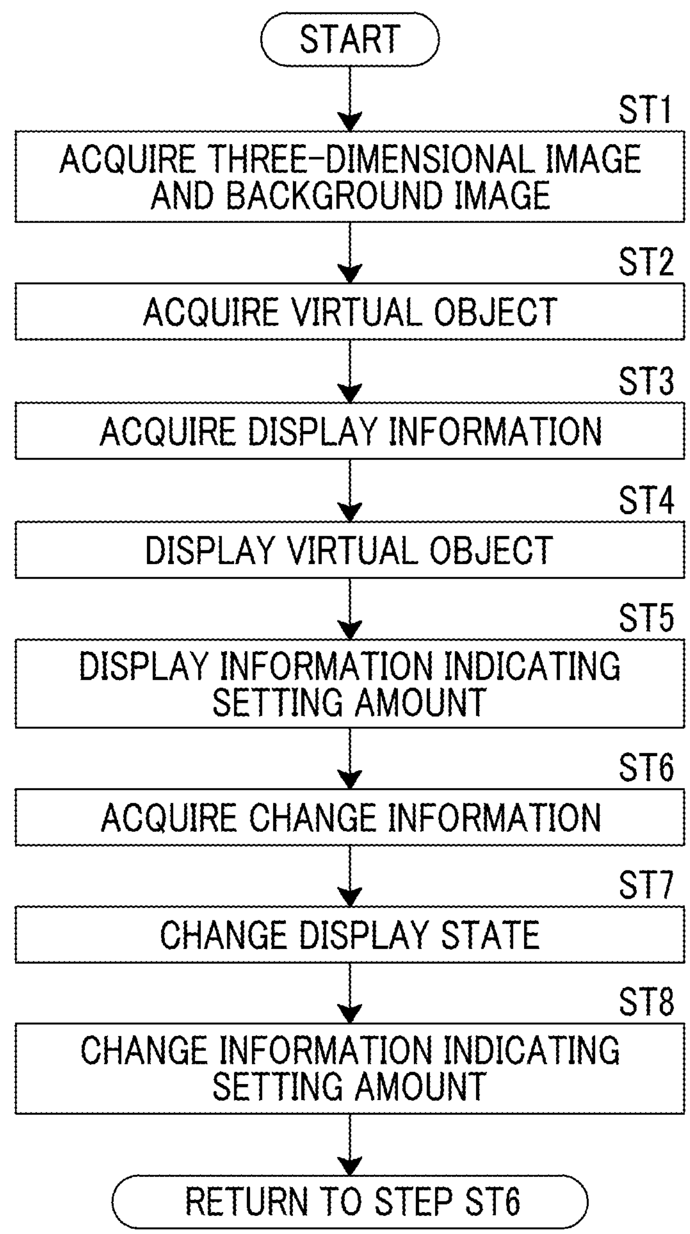
FIG. 15 is a flowchart showing the process performed in the first embodiment.

Next, the process performed in the first embodiment will be described. FIG. 15 is a flowchart showing the process performed in the first embodiment. It is assumed that the first marker 30 is placed at a location where a preoperative conference is held and the lead surgeon holds the second markers 34 and 35 in hand.

First, the image acquisition unit 21 acquires the three-dimensional image V0 and the background image B0 (step ST1), and the virtual object acquisition unit 22 acquires the virtual object S0 from the three-dimensional image V0 (step ST2). The display information acquisition unit 23 extracts the first marker image 31 showing the first marker 30 from the background image B0, and acquires display information indicating the position, the size, and the direction for displaying the virtual object S0 from the first marker image 31 (step ST3). Then, the display control unit 24 superimposes the virtual object S0 on the background image B0 using the display information, and displays the result on the display 15 (step ST4). Accordingly, each attendee of the preoperative conference wearing the HMD 1 can observe the state in which the virtual object S0 is displayed in real space. In addition, by tilting the first marker 30 or rotating the first marker 30 around the axis (z axis) perpendicular to the two-dimensional barcode in this state, the virtual object S0 can be tilted or rotated. When the virtual object S0 is displayed, the setting amount display control unit 27 displays, on the display 15, information indicating the setting amount of the display state of the virtual object S0 (step ST5).

Subsequently, the change information acquisition unit 25 extracts the second marker images 36 and 37 showing the second markers 34 and 35 from the background image B0, calculates the angle α of the straight line L2 with respect to the reference line L1, and acquires the change information of the display state of the virtual object S0 from the calculated angle α (step ST6). Then, the display state change unit 26 changes the display state of the virtual object S0 using the change information (step ST7), the setting amount display control unit 27 changes the information indicating the setting amount of the display state and displays the changed information on the display 15 (step ST8), and the process returns to step ST6.

Thus, in the present embodiment, change information for changing the display state of the virtual object S0 is acquired according to the relative relationship between the marker image 36 showing the marker 34 as a reference and the marker image 37 showing the other marker 35 other than the marker 34 as a reference, among the plurality of marker images 36 and 37 that show the second markers 34 and 35 for changing the display state of the virtual object S0 and that are included in the background image B0. Then, the display state of the virtual object S0 is changed according to the change information. Therefore, by simply changing the relative relationship between the two second markers 34 and 35, it is possible to change the display state of the virtual object S0. As a result, it is possible to accurately change the display state of the virtual object S0 according to the actual operation.

In addition, by displaying the information indicating the setting amount in the vicinity of the second marker images 36 and 37, it is possible to easily associate the display state of the second marker images 36 and 37 with the information indicating the setting amount. Therefore, it is possible to easily change the display state of the virtual object S0.

In addition, by forming the second markers 34 and 35 in a cube having information for changing the display state on each surface, the display state of the virtual object S0 can be easily changed by simply rotating or moving the cube.

In the first embodiment described above, only the lead surgeon who is the representative of the preoperative conference holds the second markers 34 and 35, and the display state of the virtual object S0 displayed on the HMD 1 of all attendees is changed by the operation of the lead surgeon. However, each attendee may hold the second markers 34 and 35 for exclusive use. In this case, by making two-dimensional barcodes to be attached to the second markers 34 and 35 different for each attendee, the second markers 34 and 35 of each attendee can be identified. For this reason, the second markers 34 and 35 are imaged by the camera 14 of the HMD 1 of each attendee, and the second marker images 36 and 37 are registered in the HMD 1 of the attendee. Then, the change information acquisition unit 25 of each HMD 1 acquires the change information only in a case where the angle α of the straight line L2 with respect to the reference line L1 acquired from the registered second marker images 36 and 37 is changed.

Then, after the virtual object S0 is displayed, the second markers 34 and 35 are imaged by the camera 14 such that the second marker images 36 and 37 are included in the background image B0 for each attendee. In a case where the attendee desires to change the display state of the virtual object S0 displayed on his or her HMD 1, the attendee changes the angle of the straight line L2 with respect to the reference line L1 described above by operating the second markers 34 and 35 owned by himself or herself, and the change information acquisition unit 25 acquires change information. Then, the display state change unit 26 changes the display state of the virtual object S0. In this case, the display state of the virtual object S0 displayed for other attendees is not changed. The setting amount display control unit 27 displays the information indicating the setting amount on the display 15. However, the information indicating the setting amount corresponds to the amount of change in the angle of the straight line L2 with respect to the reference line L1 acquired from the registered second marker images 36 and 37.

In this manner, since each attendee has the second markers 34 and 35 and registers the second marker images 36 and 37, the display state of the virtual object S0 can be changed without affecting the display state of the virtual object S0 of other attendees by changing the display state of the virtual object S0 for each attendee.

In the embodiment described above, the display state of the entire virtual object S0 is changed using the second markers 34 and 35. However, the virtual object S0 displayed according to the first embodiment includes the liver and other objects, such as arteries, veins, portal veins, and lesions included in the liver. Therefore, it is possible to change the display state for each object, such as liver, an artery, a vein, a portal vein, and a lesion. Hereinafter, this will be described as a second embodiment.

Figure 16:
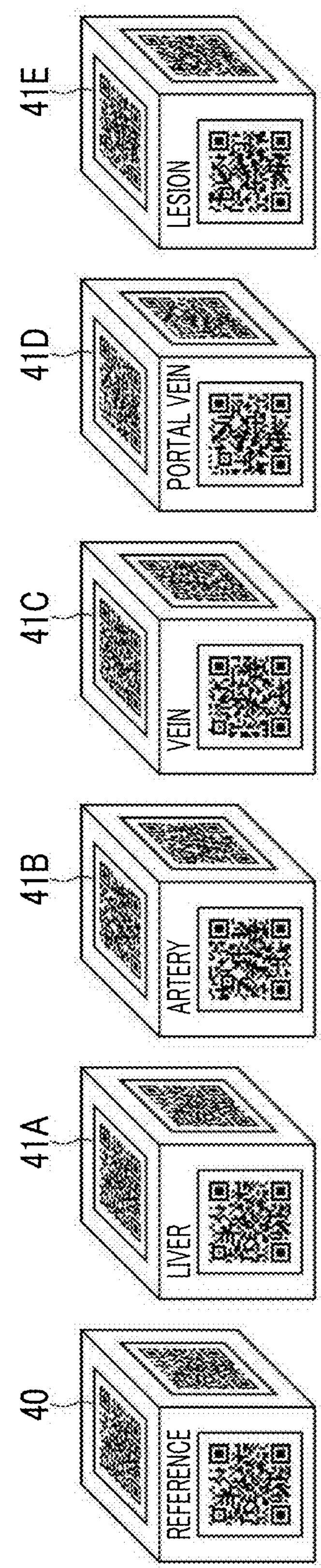
FIG. 16 is a diagram showing a second marker used in a second embodiment.
Figure 17:
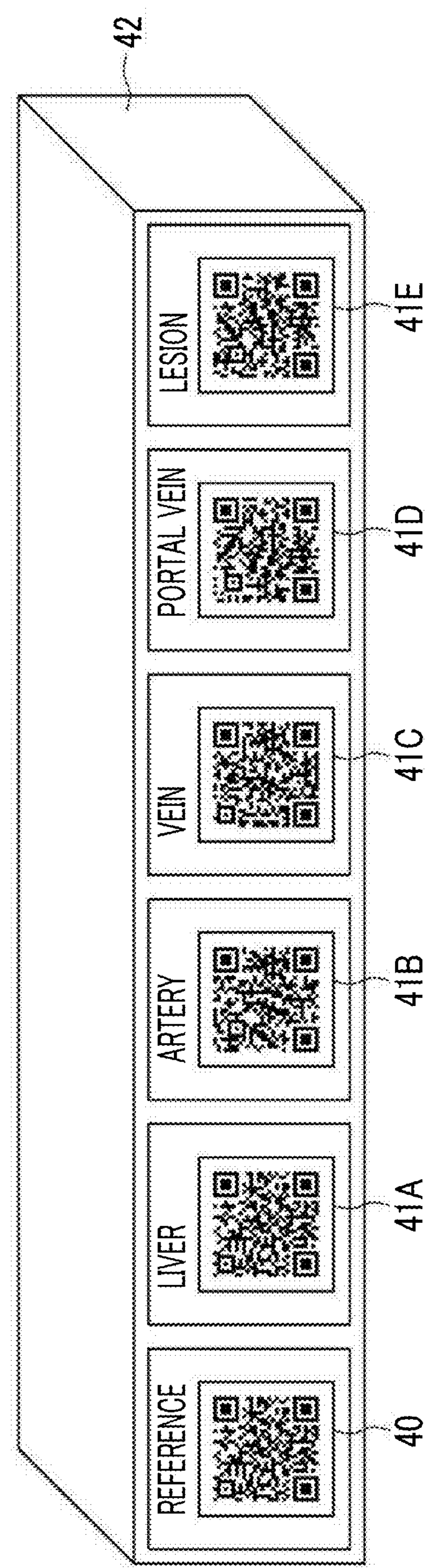
FIG. 17 is a diagram showing a second marker used in the second embodiment.

FIG. 16 is a diagram showing a second marker used in the second embodiment. As shown in FIG. 16, in the second embodiment, six second markers 40 and 41A to 41E are used. Among the six second markers 40 and 41A to 41E, the marker 40 is a reference marker, and the markers 41A to 41E are other markers. In each of the markers 41A to 41E, the name of each object is written so that it is possible to know the change of the display state of any object included in the virtual object S0. That is, the markers 41A to 41E are written as liver, artery, vein, portal vein, and lesion, respectively. The marker 40 is written as a reference so that it is possible to know that the marker 40 is a reference marker. Since it is difficult to operate such a plurality of second markers 40 and 41A to 41E in a state in which these are held by hand, it is preferable to place the second markers 40 and 41A to 41E on a table (not shown). In the second embodiment, the second markers 41A to 41E rotate only in units of 90°. In order to prevent surfaces other than the surface, to which the two-dimensional barcode on which a display state to be set is defined is attached, from being viewed, it is preferable to place the second markers 40 and 41A to 41E in a case 42 as shown in FIG. 17 and, when necessary, to extract the second markers 40 and 41A to 41E from the case 42 and change the directions of the second markers 40 and 41A to 41E so that a desired surface is imaged.

In this manner, by preparing the second markers 40 and 41A to 41E for changing the display state for each object forming the virtual object S0 and acquiring the change information (object change information) for each of the second markers 41A to 41E, that is, for each object included in the virtual object S0, each object included in the virtual object S0 can be made to have a different display state. In particular, by using a two-dimensional barcode defining non-display as a display state, a desired object cannot be displayed in the virtual object S0. Therefore, each object included in the virtual object S0 can be observed in a desired display state.

Figure 18:
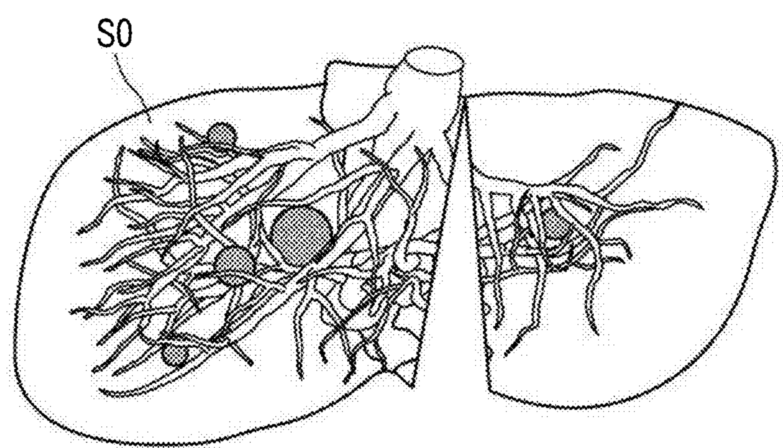
FIG. 18 is a diagram illustrating the change of the display state of a virtual object for making the liver be excised.

In the embodiment described above, a simulation motion picture of the progress of surgery may be generated in advance using the virtual object S0, and a change in the form of the virtual object S0 according to the progress of the surgery over time may be defined as a display state. In this case, by operating the second marker 35, the display state of the virtual object S0 can be changed so that the virtual object S0 changes from the state shown in FIG. 4 to a state in which the liver is excised, for example, as shown in FIG. 18.

A plurality of plans may be prepared as surgical plans, and a simulation motion picture of the progress of surgery may be generated for each plan. In this case, simulation motion pictures of different plans are associated with respective two-dimensional barcodes attached to the surfaces of the second markers 34 and 35. By displaying the two-dimensional barcode of the surface, on which a plan to be displayed is defined, on the display 15, it is possible to change the display state of the virtual object S0 based on the simulation motion picture of surgery of the plan.

In the embodiment described above, a first marker obtained by attaching a two-dimensional barcode to a plate is used. However, predetermined symbols, colors, figures, characters, and the like may be used instead of the two-dimensional barcode. In addition, predetermined objects such as an LED or a pen and an operator's finger may be used. An intersection of straight lines included in the background image B0 or the texture, such as a shining object, may be used as the first marker.

In the embodiment described above, a second marker obtained by attaching a two-dimensional barcode to a cube is used. However, other polyhedrons, such as a tetrahedron or an octahedron, may be used without being limited to the cube. In this case, two-dimensional barcodes defining different display states may be attached to the respective surfaces of the polyhedron, or the same two-dimensional barcode may be attached thereto. Without being limited to polyhedrons, a second marker obtained by attaching a two-dimensional barcode to a plate similar to the first marker 30 may be used. In this case, by rotating or moving the other marker with one of two second markers as a reference, it is possible to change the display state of the virtual object more easily.

In the embodiment described above, the display state of the virtual object S0 is changed by rotating the other marker 35 with respect to the reference marker 34 on the surface of the display 15. However, the display state of the virtual object S0 may also be changed by rotating the other marker 35 back and forth in the depth direction of the surface of the display 15. In this case, the change information may be acquired based on a change in the shape of a two-dimensional barcode attached to the other marker 35 with the reference marker 34 as a reference. The display state of the virtual object S0 may also be changed by moving the other marker 35 closer to or away from the camera 14. In this case, the change information may be acquired based on a change in the size of another marker image 37 with the reference marker image 36 displayed on the display 15 as a reference. In addition, a relative distance between the reference marker image 36 and another marker image 37 may be calculated, and the change information may be acquired based on the relative distance.

In the embodiment described above, a second marker obtained by attaching a two-dimensional barcode is used. However, two markers obtained by applying different colors to respective surfaces may be used instead of the two-dimensional barcode. In this case, change information corresponding to a combination of the colors of the two markers may be defined with one of the two markers as a reference. For example, in the case of using markers obtained by applying six colors of red, blue, green, yellow, purple, and pink to respective surfaces, change information corresponding to a combination of colors with other markers with the color of one marker as a reference may be defined such that the combination of red and red is 1.00 and the combination of red and blue is 0.75. Instead of colors, two markers obtained by applying different patterns to respective surfaces may be used. In this case, change information corresponding to a combination of patterns with other markers may be defined with a pattern of one marker as a reference. The number of markers is not limited to two, and may be three or more. In this case, change information corresponding to a combination of three or more colors or patterns may be defined with a color or pattern of one marker as a reference.

Instead of the two-dimensional barcode, markers obtained by applying numbers to respective surfaces may be used. In this case, the number may be defined by percentage, and the number of the second marker included in the background image B0 may be read so that the two second markers can be combined to display numbers, such as 100, 75, and 50, thereby acquiring the change information represented by the percentage.

In the embodiment described above, although the camera 14 is provided in the HMD 1. However, the camera 14 may be provided separately from the HMD 1. Also in this case, it is preferable to dispose the camera 14 so that a range corresponding to the viewing field of the wearer of the HMD 1 is imaged.

In the embodiment described above, the virtual object display device according to the present invention is applied to the HMD that is an immersive eyeglass type display device, but may be applied to a transmissive eyeglass type terminal device. In this case, the display 15 is a transmissive display. Accordingly, by displaying the virtual object S0 on the display 15, the wearer of the virtual object display device can observe the virtual object S0 superimposed on the real space that he or she actually watches, instead of the background image B0 captured by the camera 14 and displayed on the display 15. In this case, the camera 14 is used to image the first marker 30 for determining the position and the size for displaying the virtual object S0 and the second markers 34 and 35 for changing the display state of the virtual object S0.

In the embodiment described above, the virtual object display device according to the present invention is applied to the eyeglass type display device, but may be applied to a camera mounted tablet terminal. In this case, each attendee of the preoperative conference possesses a tablet terminal, and the background image B0 and the virtual object S0 are displayed on the display of the tablet terminal.

In the embodiment described above, the position, the size, and the direction for displaying the virtual object S0 are acquired as display information using the first marker 30, and the virtual object S0 having the size and the direction corresponding to the position where the attendee of the preoperative conference is present is displayed.

In the embodiment described above, the virtual object S0 generated from the medical three-dimensional image is displayed. However, the type of the virtual object S0 is not limited to medical use. For example, a game character or model may be used as the virtual object S0.

Hereinafter, the effect of the present invention will be described.

Since a background image is acquired by imaging the background corresponding to the viewing field of the user, it is possible to display the virtual object within the viewing field of the user. Therefore, it is possible to easily observe the virtual object.

Since at least one of the size or the direction when displaying the virtual object is included in the display information, it is possible to display the virtual object so as to have an appropriate size and/or direction.

Since the virtual object is combined with the background image and the result is displayed, the present invention is advantageous especially in displaying the virtual object using the immersive eyeglass type display device.

Since the display information is acquired from the marker image that shows a marker for displaying the virtual object and that is included in the background image by imaging the marker for displaying the virtual object, the virtual object can be displayed at the position where the marker for displaying the virtual object is disposed. Therefore, it is possible to display the virtual object at the position desired by the user in real space.

Since the display information is acquired from the reference marker image that is included in the background image by imaging the reference marker, it is possible to use both the marker for displaying the virtual object and the marker for changing the display state.

Since the information indicating the setting amount of the display state of the virtual object is displayed, it is possible to recognize the setting value of the display state of the current virtual object by viewing the displayed information indicating the setting amount. Therefore, it is possible to accurately change the display state of the virtual object.

In addition, since the information indicating the setting amount is displayed in the vicinity of a plurality of marker images indicating a plurality of markers for changing the display state of the virtual object, it is possible to easily associate the display state of the plurality of marker images with the information indicating the setting amount. Therefore, it is possible to easily change the display state of the virtual object.

Since the marker for changing the display state of the virtual object is a polyhedron having surfaces to which information for changing the display state is given, it is possible to change the display state of the virtual object more easily by rotating or moving the polyhedron.

In addition, since the eyeglass type display device is used as a display device, it is possible to display a virtual object having parallax corresponding to the left and right eyes, so that it is possible to stereoscopically view the virtual object. Therefore, it is possible to observe the virtual object in a more realistic manner.

EXPLANATION OF REFERENCES

1, 1A to 1D: head mount display (HMD)
2: three-dimensional imaging apparatus
3: image storage server
4: network
11: CPU
12: memory
13: storage
14: camera
15: display
16: input unit
17: gyro sensor
21: image acquisition unit
22: virtual object acquisition unit
23: display information acquisition unit
24: display control unit
25: change information acquisition unit
26: display state change unit
27: setting amount display control unit
30: first marker
34, 35: second marker

What is claimed is:

1. A virtual object display device, comprising:
a camera that acquires a background image;
a display unit that displays a virtual object;
a processor configured to
acquire the virtual object;
acquire display information indicating a position, at which the virtual object is displayed, from the background image;
display the virtual object on the display unit based on the display information;
acquire change information for changing a display state of the virtual object according to a relative relationship between a reference marker image showing a reference marker as a reference and each of other marker images showing other markers other than the reference marker, among a plurality of marker images that show a plurality of markers for changing the display state of the virtual object and that are included in the background image; and change the display state of the virtual object according to the change information, and wherein the changing the display state of the virtual object includes change of opacity of volume rendering, wherein the virtual object includes a plurality of objects, the processor acquires change information for the plurality of objects for changing a display state of each of the plurality of objects, the processor changes the display state for each of the plurality of objects according to the change information for each of the plurality of objects, and the processor displays information indicating a setting amount of each of the plurality of objects on the display unit for each of the plurality of objects, wherein the each of marker images other than the reference marker and each of the plurality objects correspond to tissue respectively.

2. The virtual object display device according to claim 1, wherein the background image is acquired by imaging a background corresponding to a viewing field of a user.

3. The virtual object display device according to claim 2, wherein the display unit combines the virtual object with the background image and displays a result of the combination.

4. The virtual object display device according to claim 1, wherein the display information further includes at least one of a size or a direction when displaying the virtual object.

5. The virtual object display device according to claim 1, wherein the display unit combines the virtual object with the background image and displays a result of the combination.

6. The virtual object display device according to claim 1, wherein the processor acquires the display information from a marker image that shows a marker for displaying the virtual object and that is included in the background image by imaging the marker for displaying the virtual object.

7. The virtual object display device according to claim 1, wherein the processor acquires the display information from the reference marker image that is included in the background image by imaging the reference marker.

8. The virtual object display device according to claim 1, the processor further configured to:

display information indicating a setting amount of the display state of the virtual object on the display unit.

9. The virtual object display device according to claim 8, wherein the processor displays information indicating the setting amount in vicinity of a plurality of marker images showing a plurality of markers for changing the display state of the virtual object.

10. The virtual object display device according to claim 9, wherein each of the markers for changing the display state of the virtual object is a polyhedron having surfaces to which information for changing the display state is given.

11. The virtual object display device according to claim 10, wherein the polyhedron is a cube.

12. The virtual object display device according to claim 1, wherein the virtual object is a three-dimensional image.

13. The virtual object display device according to claim 12, wherein the three-dimensional image is a medical three-dimensional image.

14. The virtual object display device according to claim 1, wherein the display unit is an eyeglass type display device.

15. A virtual object display system, comprising:

a plurality of the virtual object display devices according to claim 1 that correspond to a plurality of users, wherein the processor in each of the plurality of virtual object display devices changes the display state of the virtual object according to change information acquired by the processor of any one of the virtual object display devices.

16. A virtual object display system, comprising:

a plurality of the virtual object display devices according to claim 1 that correspond to a plurality of users, wherein the processor in each of the plurality of virtual object display devices changes the display state of the virtual object according to change information acquired by the processor of each of the virtual object display devices.

17. A virtual object display method, comprising:

acquiring a background image;

acquiring a virtual object;

acquiring display information indicating a position, at which the virtual object is displayed, from the background image;

displaying the virtual object on display unit based on the display information;

acquiring change information for changing a display state of the virtual object according to a relative relationship between a reference marker image showing a reference marker as a reference and each of other marker images showing other markers other than the reference marker, among a plurality of marker images that show a plurality of markers for changing the display state of the virtual object and that are included in the background image;

changing the display state of the virtual object according to the change information; and displaying information indicating a setting amount of the display state of the virtual object on the display unit, and wherein the changing the display state of the virtual object includes change of opacity of volume rendering, wherein the virtual object includes a plurality of objects, the change information is acquired for the plurality of objects for changing a display state of each of the plurality of objects, the display state is changed for each of the plurality of objects according to the change information for each of the plurality of objects, and the information indicating a setting amount of each of the plurality of objects is displayed on the display unit for each of the plurality of objects, wherein the each of marker images other than the reference marker and each of the plurality objects correspond to tissue respectively.

18. A non-transitory computer readable recording medium storing virtual object display program causing a computer to execute:

acquiring a background image;

acquiring a background object;

acquiring a virtual object;

acquiring display information indicating a position, at which the virtual object is displayed, from the background image;

displaying the virtual object on display unit based on the display information;

acquiring change information for changing a display state of the virtual object according to a relative relationship between a reference marker image showing a reference marker as a reference and each of other marker images showing other markers other than the reference marker, among a plurality of marker images that show a plurality of markers for changing the display state of the virtual object and that are included in the background image;

changing the display state of the virtual object according to the change information; and displaying information indicating a setting amount of the display state of the virtual object on the display unit, and wherein the changing the display state of the virtual object includes change of opacity of volume rendering, wherein the virtual object includes a plurality of objects, the change information is acquired for the plurality of objects for changing a display state of each of the plurality of objects, the display state is changed for each of the plurality of objects according to the change information for each of the plurality of objects, and the information indicating a setting amount of each of the plurality of objects is displayed on the display unit for each of the plurality of objects, wherein the each of marker images other than the reference marker and each of the plurality objects correspond to tissue respectively.

* * * * *